United States Patent
Temple et al.

(10) Patent No.: US 6,644,162 B1
(45) Date of Patent: Nov. 11, 2003

(54) MICROTOME

(75) Inventors: John Temple, Chester (GB); Ian Kerrod, Hawarden (GB)

(73) Assignee: Shandon Scientific Limited, Runcorn (GB)

( * ) Notice: Subject to any disclaimer, the term of this patent is extended or adjusted under 35 U.S.C. 154(b) by 330 days.

(21) Appl. No.: 09/706,155

(22) Filed: Nov. 3, 2000

Related U.S. Application Data (63) Continuation-in-part of application No. 09/239,103, filed on Jan. 28, 1999, now abandoned.

(30) Foreign Application Priority Data

Feb. 18, 1998 (GB) .............................................. 9803425

(51) Int. Cl.⁷ .............................................. B23D 19/00
(52) U.S. Cl. ............................ 83/703; 83/707; 83/713; 83/698.11; 83/915
(58) Field of Search ........................ 83/698.11, 915.5, 83/856, 627, 699.51, 703, 707, 713

(56) References Cited

U.S. PATENT DOCUMENTS

| | | | |
|---|---|---|---|
| 4,505,175 A | 3/1985 | Reichel | |
| 4,625,608 A | 12/1986 | Behme et al. | |
| 4,690,023 A | 9/1987 | Berleth et al. | |
| 5,099,735 A | 3/1992 | Keme et al. | |
| 5,535,654 A | 7/1996 | Niesporek et al. | |
| 5,669,278 A | 9/1997 | Metzner | |
| 5,752,425 A | 5/1998 | Asakura et al. | |
| 5,851,213 A | 12/1998 | Berleth et al. | |
| 5,906,148 A | 5/1999 | Aihara et al. | 83/414 |
| 6,058,824 A | 5/2000 | Neymeyr | 83/698.21 |

FOREIGN PATENT DOCUMENTS

| | | |
|---|---|---|
| DE | 2 134 278 A | 8/1984 |
| DE | 2 145 241 A | 3/1985 |
| DE | 195 28 180 A1 | 2/1997 |
| WO | WO 97/26524 | 7/1997 |

OTHER PUBLICATIONS

Sorvall MT6000 Ultramicrotome Product Information Brochure; DuPont Company, Clinical & Instrument Systems, USA; XP–002104374; 1984.

*Primary Examiner*—M. Rachuba
(74) *Attorney, Agent, or Firm*—Fulwider Patton Lee & Utecht, LLP (57) ABSTRACT

An automatic microtome is disclosed which comprises a base, a knife-holder mounted on the base for supporting a microtome knife, a specimen holder mounted for longitudinal movement relative to the base towards and away from the knife-holder and also mounted for transverse movement relative to the knife holder for displacing a specimen held by the specimen holder relative to a knife mounted in the knife holder for cutting sections from such specimen. The knife holder is mounted directly on the base without provision for adjustment of the position of the knife holder on the base such as to vary the location of the knife edge in relation to said edge, and the specimen holder is designed to provide enhanced stability over a wide range of longitudinal positions the specimen holder. Thus, the specimen holder comprises a slide mounted for longitudinal movement in a bearing arrangement including first and second bearing elements at longitudinally spaced positions along the slide, and limiting transverse movement of the slide in one direction and a third bearing element at a longitudinal position intermediate the first-mentioned longitudinally spaced positions and biased towards the slide so as to urge the latter into engagement with said first and second bearing elements. The knife holder and base have cooperating arcuate bearing surfaces permitting angular movement of the knife holder relative to the base about the axis of curvature of the bearing surfaces with concomitant sliding movement of one of said arcuate surfaces over the other. A locating device is adjustably secured to the knife holder for cooperation with a datum provided on the base to ensure that with the locating device fixed to the knife holder the angular position of the knife holder on the base at which the locating device cooperates with the datum can readily be established.

10 Claims, 8 Drawing Sheets

MICROTOME

RELATED APPLICATIONS

This is a continuation in part of Ser. No. 09/239,103 filed Jan. 28, 1999 abandoned.

BACKGROUND OF THE INVENTION

1. Field of the Invention

THIS INVENTION relates to microtomes, that is to say to devices used for cutting thin sections from specimens for, for example, microscopic examination. The invention relates, more particularly, to microtomes which are to some degree mechanised or automatic in operation.

2. Description of Related Art

Mechanised or automatic microtomes are known which comprise a rigid base, a knife holder secured to said base, a microtome knife secured in the knife holder and a specimen support, on which a specimen to be sectioned is mounted, the specimen support being mounted for movement relative to the base so as to cause a specimen mounted on the specimen support to execute a transverse movement with respect to the knife blade, appropriate to the cutting of slices or sections from the specimen. Generally, in such known microtomes, the specimen support is also mounted for advancing and retracting movement relative to the knife for the cutting of successive sections or slices from the specimen and for withdrawing the specimen holder from the region of the knife for mounting a fresh specimen and so on.

In known microtomes of this character, the microtome knife is supported in a knife holder which is adjustable in position to vary the proximity of the knife to the specimen holder. This known arrangement has, however, the disadvantage that the knife is not always supported as rigidly as it might be, with consequent deficiencies in the operation of the microtome.

SUMMARY OF THE INVENTION

It is an object of the invention in one of its aspects to provide an improved microtome in which the firmness of mounting of the microtome knife can more readily be assured than in the past.

According to this aspect of the invention there is provided a microtome comprising a base, a knife-holder mounted on the base for supporting a microtome knife, a specimen holder mounted for longitudinal movement relative to the base towards and away from the knife-holder and also mounted for transverse movement relative to the knife holder for displacing a specimen held by the specimen holder relative to a knife mounted in the knife holder for cutting sections from such specimen, wherein the knife holder is mounted directly on the base without provision for adjustment of the position of the knife holder on the base such as to vary the location of the knife edge in relation to said edge.

In addition to the rigidity secured in accordance with this aspect of the invention, the fixed knife mounting, in the preferred embodiment makes for ease of cleaning the instrument.

The invention in another of its aspects provides improved means for ensuring reproducibility of the microtome knife angle with respect to the specimen to be sectioned, between replacements or other adjustments of the knife relative to the remainder of the microtome. It is known that, in operation of mechanised or automatic microtomes, in particular, different angles are required for the various plates or knives used to compensate for different facet angles, embedding mediums and materials to be sectioned. Routine practice requires the setting of only one angle on the knife holder, which angle can be maintained or reproduced when, for example, the knife holder is removed for cleaning or replaced with an alternative holder. In conventional microtomes, it is normal to utilize a knife holder having a base which is removable from the frame or base structure of the microtome and which is replaceable on such structure. Accordingly, in normal practice, the knife holder and its base are removed together from the remainder of the machine and replaced together, so that the knife angle is thereby retained. In a microtome in accordance with the first aspect of the invention, where the knife holder, or at least the knife holder base, is a fixed part of the base or frame of the microtome as a whole, the procedure described above in relation to conventional microtomes is not available and it is an object of the present invention, in another of its aspects, to provide a means of maintaining or reproducing a predetermined angle of the microtome knife when mounted in the microtome, which means is not confined to microtomes having knife holders with bases removable from the remainder of the microtome with the knife holder.

In accordance with this further aspect of the invention, accordingly, there is provided a microtome comprising a knife holder and a knife holder support having cooperating arcuate bearing surfaces permitting angular movement of the knife holder relative to the knife holder support about the axis of curvature of said bearing surfaces with concomitant sliding movement of one of said arcuate surfaces over the other, wherein a sensor or locating device is adjustably secured to the component providing one of these bearing surfaces, for cooperation with a datum provided on the component providing the other of these arcuate bearing surfaces, to ensure that with said sensor or locating device fixed to said component providing said one of said bearing surfaces the angular position of the knife holder on the knife holder support at which said sensor or locating device cooperates with said datum can readily be established.

The invention in another of its aspects relates to the mounting of the specimen holder in a microtome. In microtomes in which the specimen holder is advanced towards and is retractable from the knife, it is important, for proper sectioning of the specimen, that the specimen support, whilst being adjustable in position relative to the remainder of the microtome structure, be supported rigidly in such a way as to resist effectively any unintended displacements and deflections. This is particularly so in the case of the microtome in accordance with the first-noted aspect of the invention in which the position of the microtome blade is fixed and in which the specimen holder must therefore be capable of being advanced over a greater linear range towards and away from the blade than in microtomes in which there is the possibility of mounting the blade holder nearer to or further from the structure for which the specimen support is supported.

According to this aspect of the invention, accordingly, there is provided a microtome comprising a base, a knife-holder mounted on the base for supporting a microtome knife and a specimen holder mounted for longitudinal movement relative to the base towards and away from the knife holder, wherein said specimen holder comprises a slide mounted for longitudinal movement in a bearing arrangement including first and second bearing elements at longitudinally spaced positions along the slide, and limiting transverse movement of the slide in one direction and a third bearing element at a longitudinal position intermediate the first-mentioned longitudinally spaced positions and biased towards the slide so as to urge the latter into engagement with said first and second bearing elements.

The features according to this aspect of the invention are of particular utility in relation to a microtome in accordance with the first aspect of the invention, where the fixed knife position requires the specimen to be moved up to the knife rather than vice versa. To allow for a range of block depths or of specimen depths to be sectioned, enough specimen travel must be allowed between specimen and knife position. This implies that the specimen may be required to be sectioned with the specimen holder supporting the specimen at or near to its full extension from the structure from which the specimen holder is adjustably supported, so that the need for stable support of the specimen holder is particularly acute.

According to a yet further aspect of the invention, there is provided a microtome comprising a base, a knife fixed with respect to the base, a specimen holder mounted for longitudinal movement relative to the base towards and away from the knife, motor means for advancing and withdrawing the specimen holder automatically to controllable extents, and automatic control means capable of advancing or retracting the specimen holder to a pre-set position upon execution of a command operation.

This feature enables the rapid positioning of the specimen from the loading/unloading position to the trimming/sectioning position. In microtomes in accordance with the first-noted aspect of the invention, in particular, the fixed knife position means that the specimen must always move up to and away from the knife, rather than vice versa and the auto-load feature speeds up the processing between blocks or specimens when the correct "memory" position is set and ideally ensures no clashes between block and knife.

BRIEF DESCRIPTION OF THE DRAWINGS

Embodiments of the invention are described below by way of example with reference to the accompanying drawings in which.

DETAILED DESCRIPTION OF THE PREFERRED EMBODIMENTS

Figure 3:
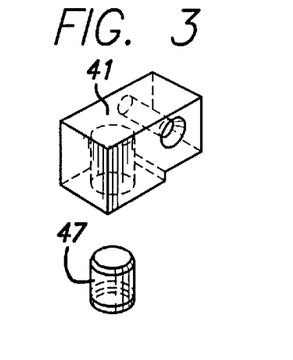
FIG. 3 is an exploded detail view showing part of a knife angle setting mechanism.

Referring to the drawings, a microtome comprises a main frame or base 9 which may, for example, be a metal casting, and upon which the remaining components of the microtome are mounted. At one end of the base 9 is mounted a knife holder assembly indicated generally at 20 and comprising a knife holder base 11 which is fixedly secured to the base 9 and on which is adjustably secured a knife holder block 12, on which a microtome knife proper, indicated at 22, is removably secured in manner known per se. As best shown in FIG. 3, the knife holder block 12 affords two, laterally spaced upstanding pillars 12a defining therebetween a space within which a specimen can be located and displaced for sectioning by the knife 22, the cutting edge of which defines, in effect the upper edge of an end wall of this space, which space IS spanned by a specimen section deflector 24 secured to the pillars 12a.

Figure 1:
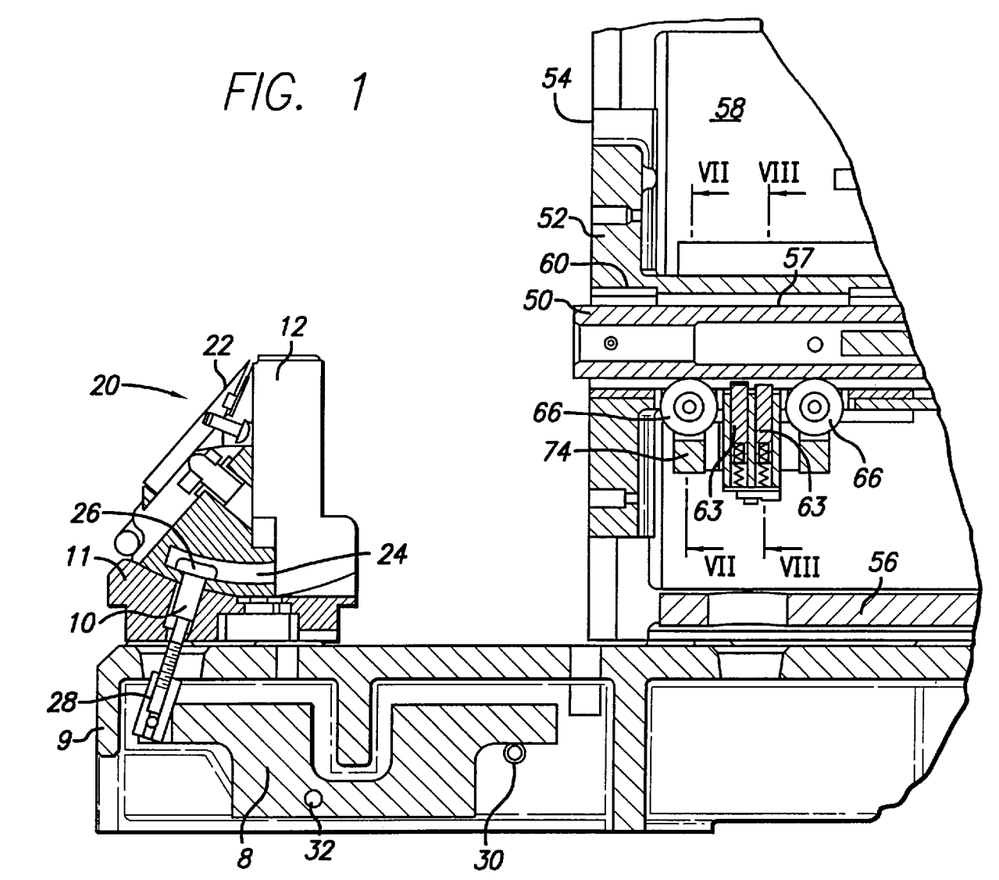
FIG. 1 is a view in vertical longitudinal section of part of a microtome embodying the invention.
Figure 2:
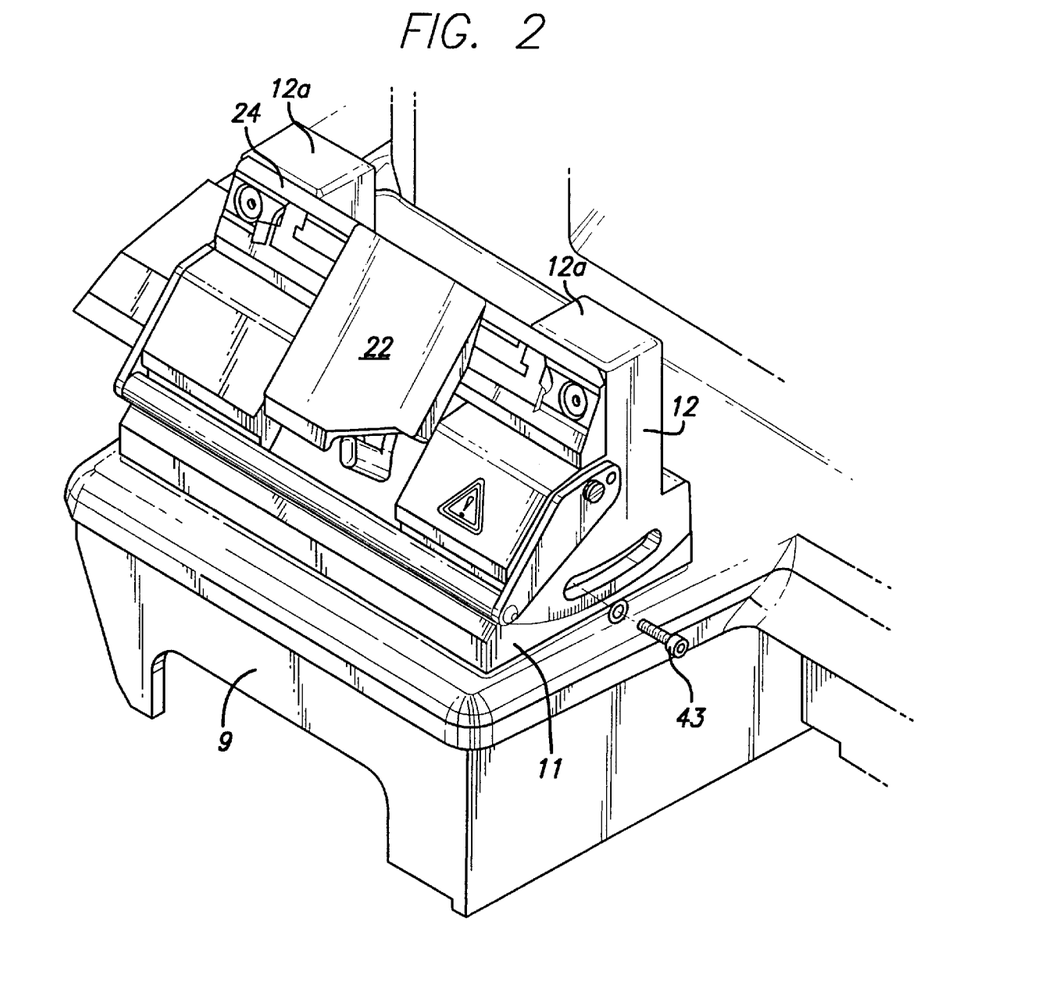
FIG. 2 is a perspective view of part of the microtome of FIG. 1.

The knife holder base 11 may be integral with the base 9 or may be secured fixedly thereto, for example by bolts (as illustrated). The knife holder base 11 has an upwardly facing concave cylindrical bearing surface which mates with a complementary convex bearing surface forming the underside of the knife holder block 12, an arrangement permitting angular adjustment of the knife holder block 12 relative to the base 11 about a horizontal transversely extending axis. The centre of curvature of these cooperating part-cylindrical bearing surfaces coincides with the position of the cutting edge of the blade 22 so that angular adjustment of the block 12 with concomitant sliding rotational movement between the convex bearing surface on the block 12 and the concave bearing surface on the base 11 does not significantly alter the position of the cutting edge of the blade 22. Except when angular adjustment is required, the block 12 is fixedly secured on the base 11 by mean of a retaining element or plunger 10 in the form of an elongate bolt which extends slidably through an aperture in frame 9 and through a bore in the base 11, through the mouth of a T-section slot 24 which extends within the knife holder block 12 along an arc about the centre of curvature of the convex lower face of the block, the slot 24 lying adjacent said lower face, the narrower mouth of the slot 24, defining the upright of the "T", opening onto said lower convex surface. The slot 24 extends from the forward end of the block 12. The bolt 10 has a neck portion extending through said narrow mouth and an enlarged head 26 within the slot 24, providing a peripheral flange which bears upon the ledges, defined by the slot 24, lying on opposite sides of the narrower portion of the slot through which the neck portion of bolt 10 extends. The lower end of the bolt 10 is screw-threadedly engaged in a nut 28 which is pivotally connected to the end of one arm of a lever 8 which is mounted within a recess in the underside of the base 9 and pivots on a transverse pivot pin 32 extending through the base 9. The lever 8 has another arm, remote from nut 28 and which is acted on by an eccentric 30 on a horizontal transversely extending shaft (not shown) which is rotatable manually or by motor means (not shown) for pivoting the lever 8 about the pivot 32, in the plane of FIG. 1, anti-clockwise as viewed in the figure to draw the bolt 10 downwardly and thus pull the block 12 down firmly against the base 11, or clockwise to release the bolt 10 and lift the bolt 10 sufficiently to release lease the downward pressure on the edges of slot 24 and thus permit angular adjustment of the knife holder block 12 relative to the base 11. The arrangement described enables a range of similar knife holders 12 to be attached to the base and angled to achieve optimum sectioning performance, with the cutting edge of the blade being always at the centre of the radius of curvature of the surfaces of the block 12 and base 11 whereby said cutting edge is always at a fixed position in relation to the remainder of the microtome.

In order to allow ready re-establishment of the desired angular position of the block 12 and knife 22, relative to base 11, about the axis of curvature of the mating bearing surfaces of the block 12 and base 11, for example after the knife holder block 12 has been temporarily removed from the base 11 and replaced thereon, an adjustable locating device or "memory" feature is provided, as described below. Thus, located in a further slot 41*a* extending arcuately about the centre of curvature of the cooperating bearing surfaces of the block 12 and base 11 and which slot likewise opens onto the bearing surface of block 12, is a slider block 41 shown in perspective FIG. 3. Block 41 has a transverse screw-threaded bore to receive a complementary screw-threaded shank of a bolt 43 which extends through an arcuate slot 43*a* in the side face of the knife holder adjacent the slot 41*a* which receives the block 41. The last-noted arcuate slot 43*a* opens into the adjoining side wall of the slot 41*a* which receives the block 41. The arcuate slot 43*a* receiving the bolt 43 is rebated to receive the enlarged head of the bolt 43 which may, as illustrated, be of the Allen type, i.e. of the type having a polygonal—(typically hexagonal) section recess extending axially into the bolt head, to receive a key of complementary cross-section for turning the bolt. Thus, with the bolt 43 slackened, the block 41 can be adjusted to any desired one of a range of positions along the slot which accommodates it and can be secured in that position by tightening the bolt 43.

Figure 4:
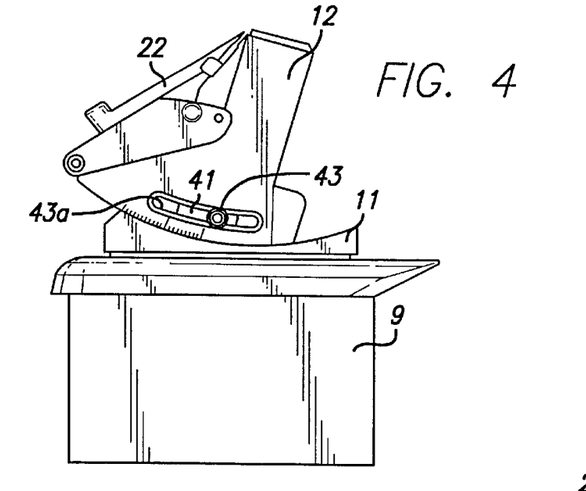
FIGS. 4 and 5 are side elevation views showing the knife holder mounting of the microtome of FIGS. 1 to 3, FIG. 5 showing a detail partly in section.
Figure 5:
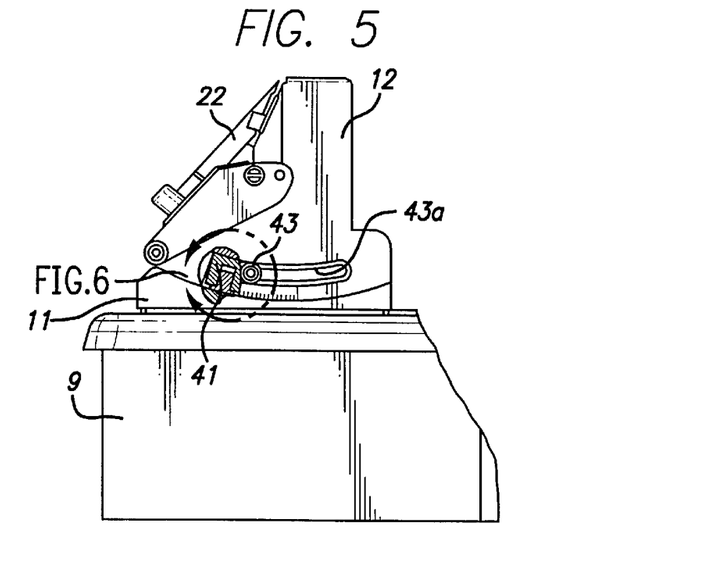
Figure 6:
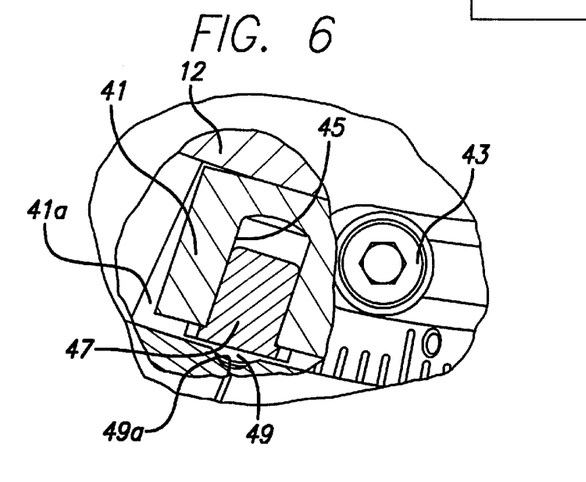
FIG. 6 is a view to an enlarged scale of the detail in FIG. 5.

As best shown in FIG. 6, the block 41 has a blind bore 45 extending upwardly from its lower surface, the bore 45 being screw-threaded and receiving a correspondingly screw-threaded insert 47 in which a steel ball 49 is held captive, together with a biasing spring (not shown) urging the ball 49 downwardly to project downwardly from the block 41 for engagement with the upwardly presented surface of the base 11. More particularly, the bearing surface of the base 11 has a pit or slot 49*a* therein in which the ball 49 engages in one angular position of the knife holder. The last-noted angular position is, of course, determined by the position of the block 41 along its slot. In order to facilitate adjustment of the knife holder to a desired angle, the adjoining side face of the block 12 is graduated in degrees, as illustrated in FIGS. 4 to 6, and the adjoining edge face of the base 11 is provided with a reference mark cooperating with these graduations. It will be appreciated that, once the position of the block 41 in its slot has been set, the correct angular position of the block 12 with respect to the base 11 can be found simply by rotating the block 12 on the base 11 until the ball 49 engages in the slot or pit 49*a* in the upper bearing surface of the base 11.

The block 41, together with the insert 47, ball 49 and its biasing spring and the bolt 43 together form an adjustable sensor or locating device adjustably secured to the block 12, whilst the slot or pit 49*a* in the bearing surface of the base 11 constitutes a datum for cooperation with the adjustable locating device and in particular for cooperation with the ball 49.

Figure 5A:
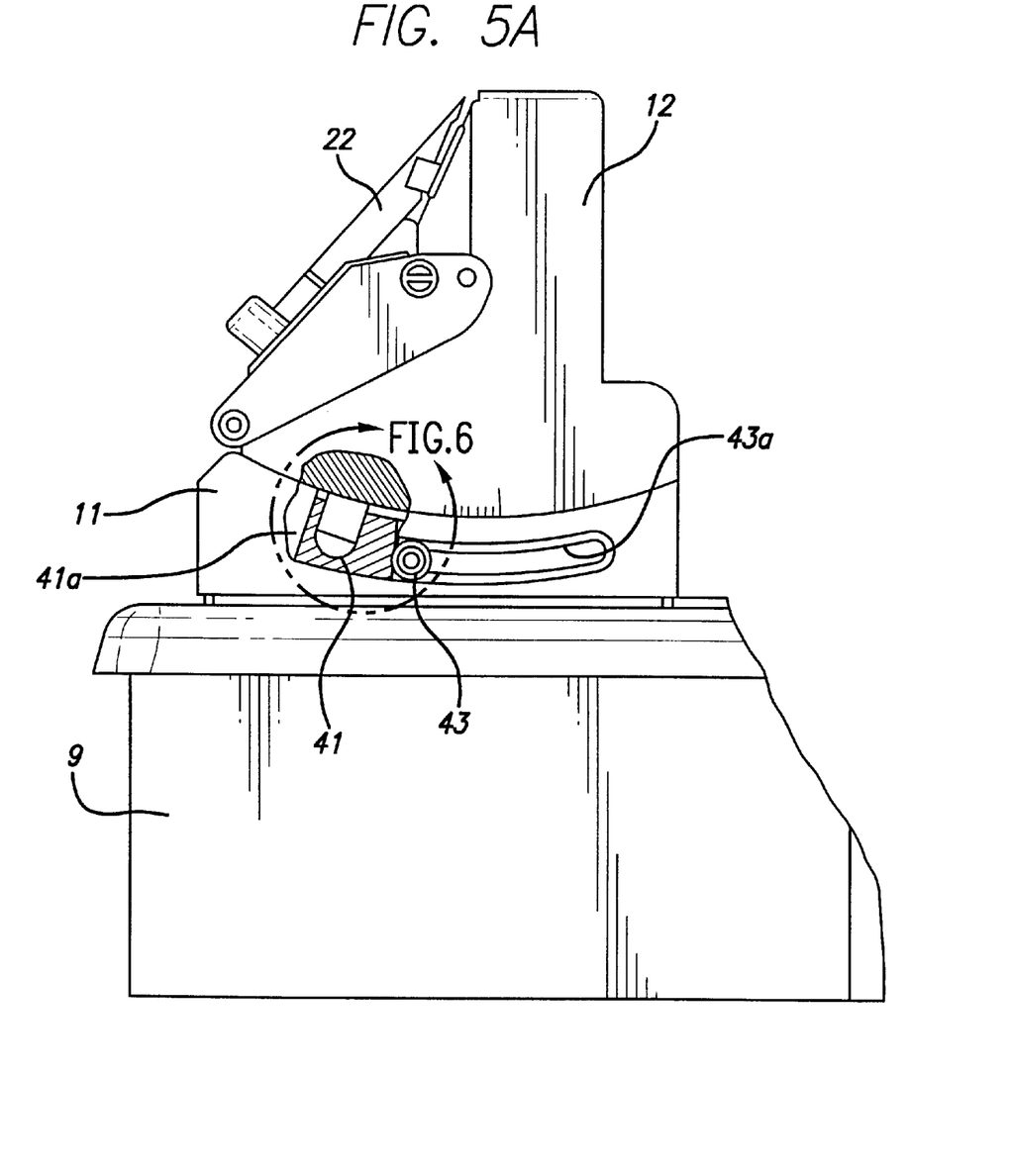
FIG. 5A is side elevation view, corresponding to FIG. 5, of a variant and likewise showing a detail partly in section.
Figure 6A:
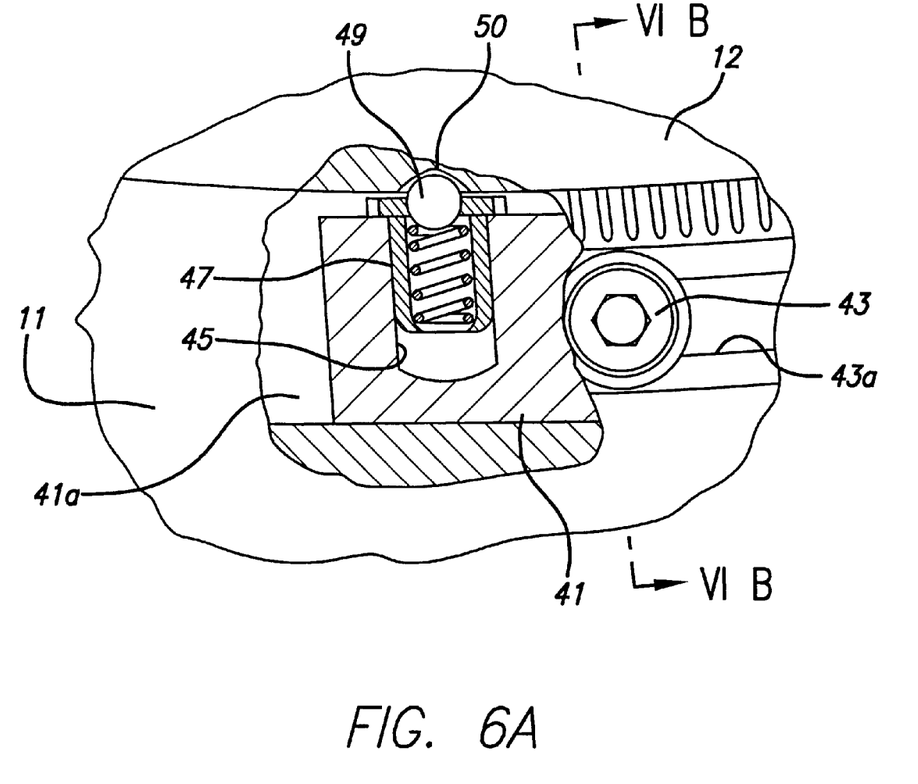
FIG. 6A is view, similar to FIG. 6, of the detail in FIG. 5A to an enlarged scale.
Figure 6B:
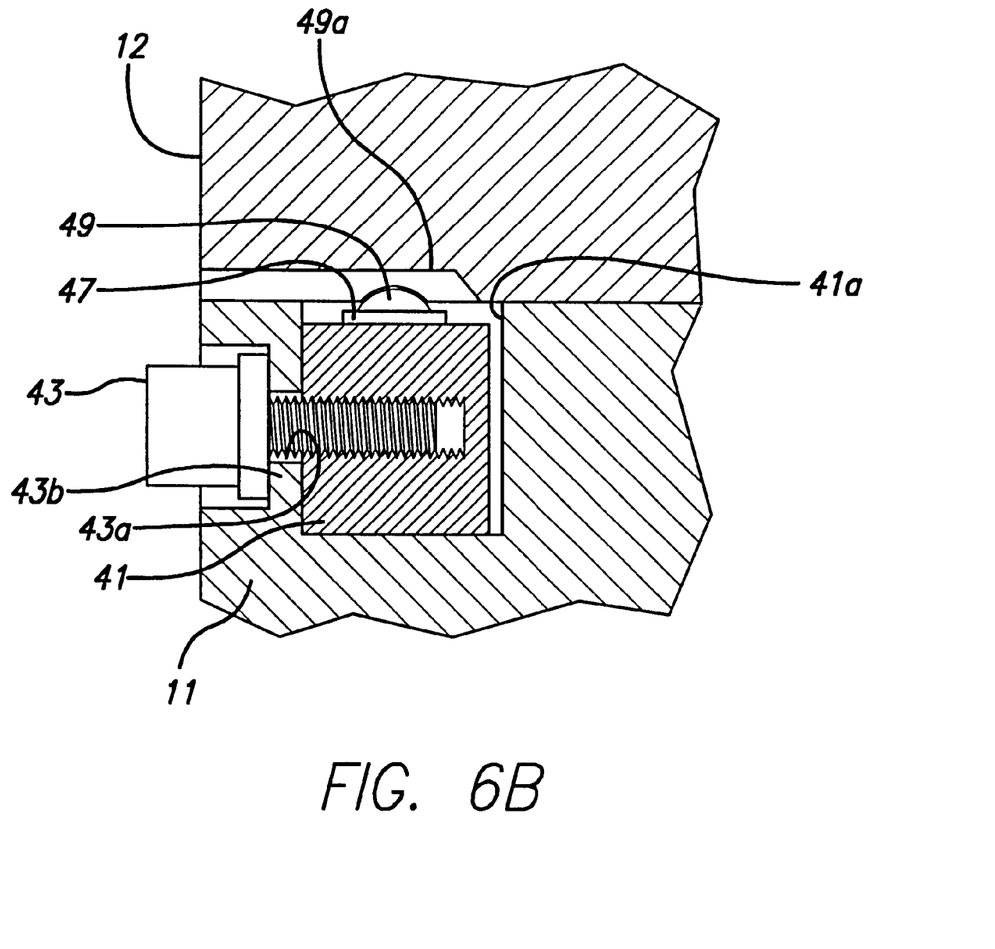
FIG. 6B is view in section along the line B—B in FIG. 6A.

In a variant, illustrated in FIGS. 5A, 6A and 6B, the locating device is adjustably secured to the base 11 and the pit or slot 49*a* is provided on the bearing surface of the knife holder block 12. Thus, in the variant of FIGS. 5A, 6A and 61B, the arcuate slot 41*a* which receives the slider block 41 and which again extends arcuately about the centre of curvature of the cooperating bearing surfaces of the block 12 and base 11, is formed in the bearing surface of the base 11 and the shank of the bolt 43 extends through arcuate slot 43*a* in the side face of the base 11 in this variant. The arcuate slot 43*a* is again rebated to receive the enlarged head of the bolt 43. Corresponding parts in FIGS. 5A, 6A and 6B corresponding to parts in FIGS. 1 to 6 have corresponding reference numerals.

It should be noted that the sectional view of FIG. 6B would equally be a representation of a vertical section through the longitudinal axis of bolt 43 in FIGS. 5 and 6 if the figure were simply inverted (i.e. rotated through 180°) and the references 11 and 12 simply transposed. In both the arrangement of FIGS. 1 to 6 and in the variant of FIGS. 5A, 6A and 6B, when the bolt 43 is tightened to fix the locating device 41, 47, 49, etc. in a desired position, the effect is to clamp the thinner portion 43*b* (see FIG. 6B) of the wall of the block of the block 12 or base 11 through which the shank of the ball 43 extends between the block 41 and the head of the bolt 43, or where a washer is provided around the shank of the bolt 43 between the head of the bolt 43 and the wall 43*b*, between that washer and the block 41. The block 41 is thus held in the selected location by friction until such time as the bolt 43 is unscrewed releasing the clamping pressure applied to the wall portion 43*b* and allowing adjustment of the block 41 along its slot 41*a*.

The bolt 43 retains the block 41 in position in its slot when the knife holder block 12 is removed from the base 11 and thus serves to "memorize" the appropriate angular setting. Thus, when the knife holder block 12 is returned to the base 11, it is simply necessary for the operative setting up the microtome to place the knife holder block 12 with its bearing surface on that of the base 11 and to rotate the knife holder substantially about the axis of curvature of its bearing surface until the ball 49 meets and drops into the slot 49*a*, an occurrence which the operative can readily detect by feel and which additionally provides an added resistance to further rotation of the knife holder block, providing the operative with an unequivocal indication that the correct position has been reached, at which the knife holder block may then be clamped by means of the bolt 10 and lever 8. The datum 49*a* preferably takes the form of a V-section slot or groove extending longitudinally parallel with the axis of curvature of the bearing surfaces, and thus also parallel with the axis of bolt 43, so as to accommodate slight movements of the block 41 in directions parallel with said axes during clamping and unclamping of the block by tightening slackening the bolt 43.

Referring again to FIG. 1, the microtome includes a specimen carrier, shown only partly in FIG. 1, the portion shown comprising a straight mounting tube 50 to the forward end of which is secured, in use, a specimen mounting arrangement (not shown but known per se), including a mounting plate for holding a specimen to be sectioned. In use of the microtome, the specimen to be sectioned is mounted on the mounting plate, in manner known per se, by means of a vice (not shown) and an orientation head (not shown), the vice and orientation head being likewise known per se. The specimen tube 50 extends with its longitudinal axis horizontally, through a support or carriage 52 which is movable in a vertical plane, parallel with the cutting edge of the blade 22, by means not shown, to effect sectioning of a specimen carried by the tube 50.

The carriage 52 includes a generally vertically extending end flange 54, (constituting the mounting plate referred to above), guided for vertical sliding movement in guideways at the front of a housing, indicated at 56, secured to the microtome base 9. The specimen tube 50 has, externally, the form of a smooth cylinder from which surface portions have been removed, a first such surface portion comprising an upper longitudinal portion defined by a flat 57, horizontally extending, extending longitudinally along the top of the tube, and a second such portion comprising a groove 64, extending along the bottom of the tube, diametrally opposite the flat 57, is a groove 64 of truncated inverted V-section. The tube 50 is guided for horizontal sliding movement towards and away from the microtome knife, through a horizontal bore in a stem portion 58 of the carriage 52, in two sintered cylindrical oil-filled bushes 60 fitted in respective ends of the bore in stem portion 58, adjacent respective open ends of said bore.

Figure 7:
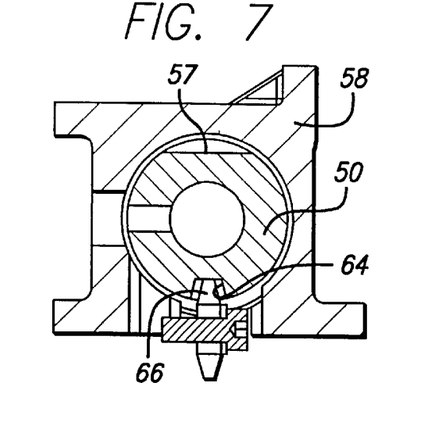
FIG. 7 is a partial view in section on the line VII—VII in FIG. 1.
Figure 8:
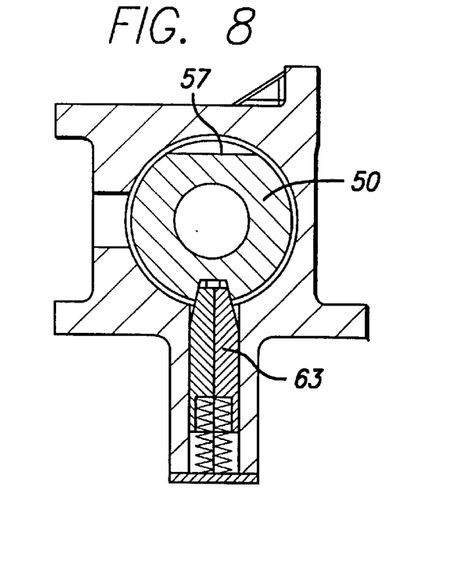
FIG. 8 is a view in cross section along the line VIII—VIII in FIG. 1.
Figure 9:
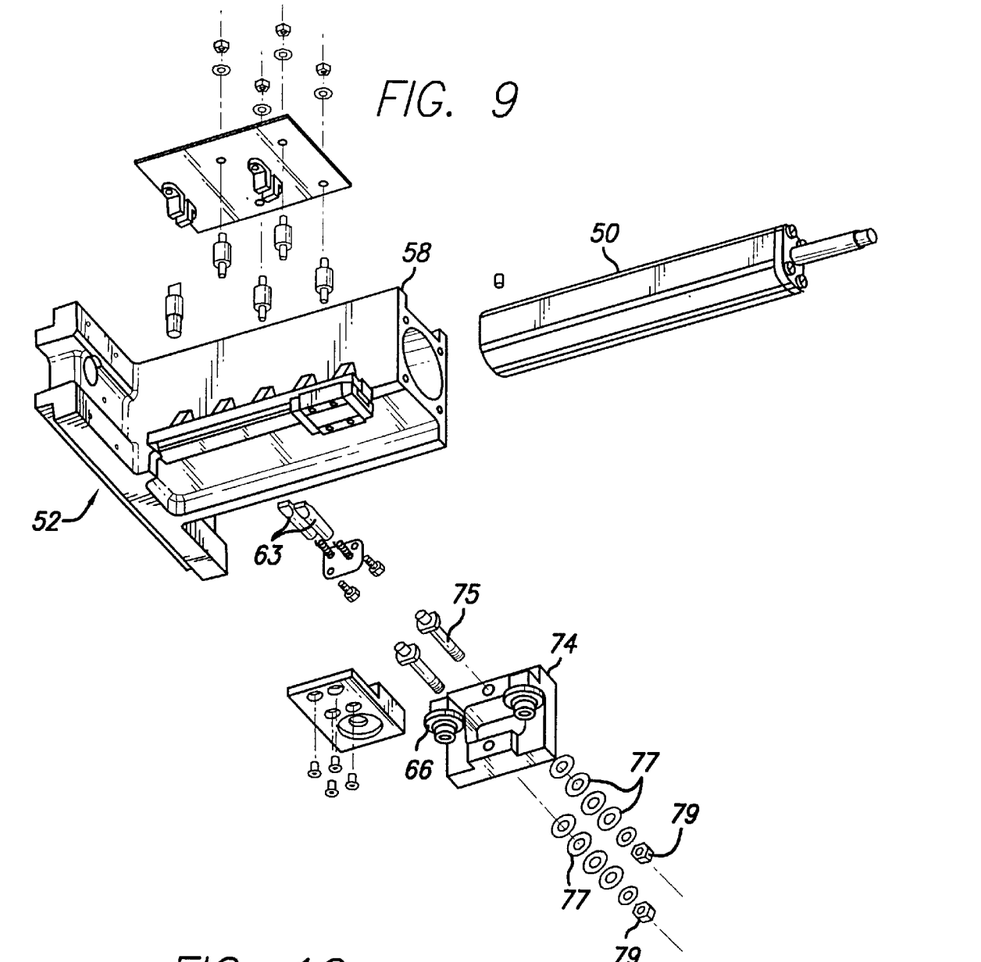
FIG. 9 is an exploded view of part of the microtome of FIGS. 1 to 8.
Figure 10:
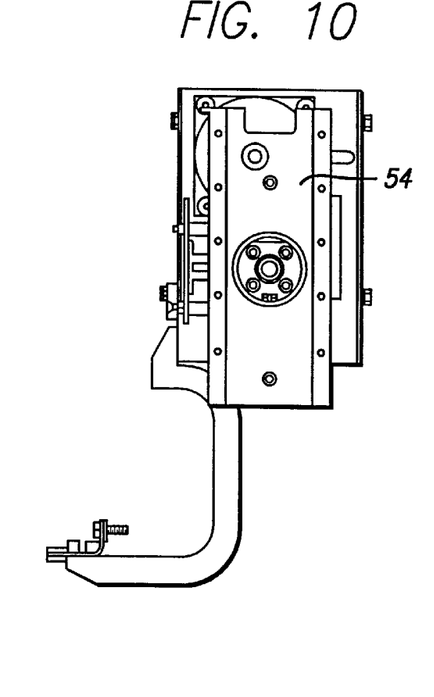
FIG. 10 is an end view of the part shown in FIG. 9, in an assembled condition.
Figure 11:
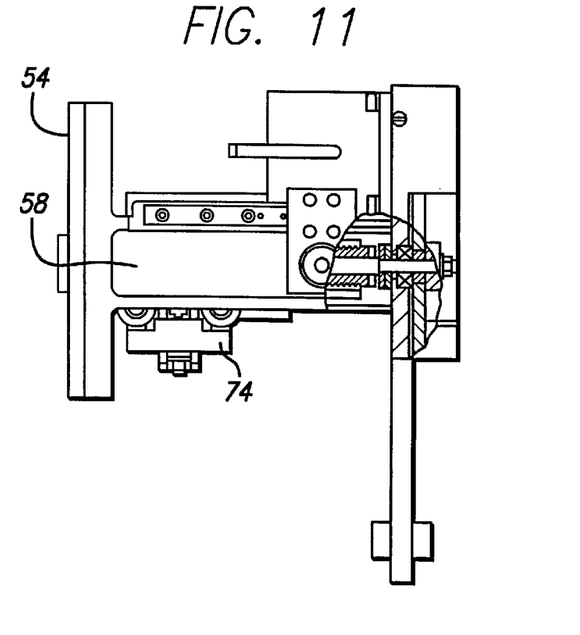
FIG. 11 is a side elevation view of the last-noted part in the assembled condition and FIG. 12 is schematic side elevation view of the microtome.

In the groove 64 run two wheels 66 which are spaced apart longitudinally of the stem 58. The wheels 66 are rotatably mounted, for rotation about respective horizontal axes, perpendicular to the longitudinal axis of the tube 50, in an undercarriage assembly 74 (see also FIG. 9) extending downwardly from a fixed portion of the microtome structure. As shown in FIG. 9, screw-threaded studs 75 extend downward from said fixed portion of the microtome through respective bores in a chassis of the undercarriage assembly 74, said chassis being supported and urged upwardly by a stack of disc spring washers 77 on each of said studs, retained by a respective nut 79 at the lower end of each said stud. Thus, the undercarriage assembly is urged, by the spring washers, upwardly against the specimen tube 50, which in turn is forced upwardly against the upper regions of the bores through the bushes 60 and, in particular, against the portions of these bushes lying directly adjacent the longitudinal flat 57 along the top of the specimen tube. As a result, and by virtue of the mutual inclination of the portions of the bushes engaging the specimen tube adjacent said flat 57, the specimen tube is centred in the bushes so as to resist lateral horizontal displacement therein. The wheels 66 on the undercarriage 74 rotate as the specimen tube 50 advances and retracts. The disc springs 77 allow some movement of the undercarriage 74 to compensate for any misalignment and any wear in the system. The flat 57 along the top of the specimen tube 50 has the effect that the specimen tube 50 is in fact supported on three localized areas—the two areas at the sides of the top flat 57 and the preloaded undercarriage wheels 66 running in the groove 64. As shown in FIG. 7 and also in FIGS. 1 and 9, two plungers 63 extend vertically, are guided closely in respective vertical bores in the lower wall of the stem 58 and have tapered noses which engage respective side walls of the inverted V-section groove in the underside of the specimen tube 50. The plungers 63 are urged vertically upwardly by respective springs. These plungers 63 act to prevent rotational movement of the specimen tube about its longitudinal axis and take up any rotational play which the specimen tube 50 might otherwise have in its bearings 60.

The specimen tube 50 can be longitudinally advanced and retracted automatically, for example by means of a feed screw arrangement driven by an electric motor controlled by electronic control means, for making the feed movements between successive cutting strokes for cutting successive thin sections from a specimen and for making the relatively gross movements required to move a specimen from a position withdrawn from the knife at which the specimen is mounted, for example, to a position adjacent the knife in preparation for sectioning.

The preferred embodiment of the invention preferably has a block auto-load feature as described below.

The block auto-load feature is an automatic system to assist the user in the routine of mounting specimen blocks in the microtome at a safe distance from the knife, bringing the block to the knife position for trimming and/or sectioning, and returning the block to unload from the microtome at a safe distance from the knife, ready to re-load.

This auto-load is likely to be of particular use in rotary microtomes.

Figure 12:
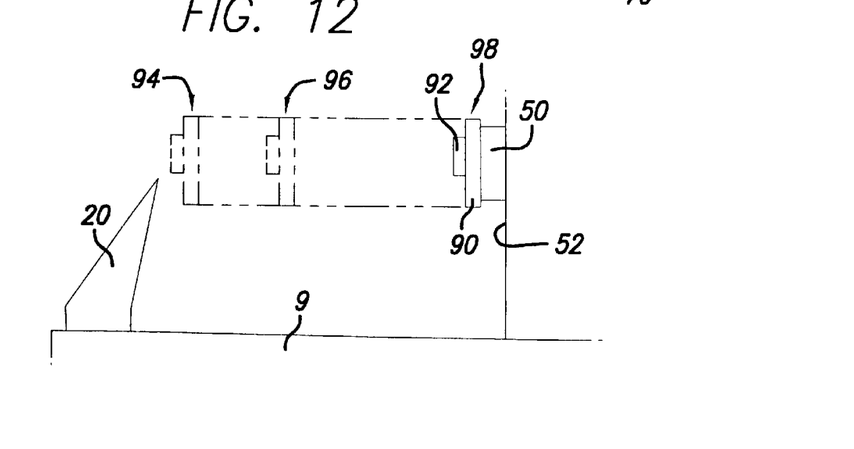

Referring to the schematic diagram forming FIG. 12, the auto-load feature in the preferred embodiment is controlled by two keys (not shown) on a control unit (not shown) controlling a microcontroller or microcomputer (not shown) included in the control means referred to and which may be installed within the microtome casing. One of these two keys is a MEMORY key, used to set a position (94 in FIG. 12) of the specimen mounting plate 90 (carried by the specimen tube 50) to which all succeeding specimens/blocks of the same depth may be advanced, to be ready for trimming/ sectioning. The control system may include a facility for advancing and retracting the specimen tube 50 under manual control, and this may be used to place the specimen tube in a desired "memory" position 94, suitable for commencement of cutting of a specimen 92 mounted on plate 90. This position may then be stored by operation of the MEMORY key referred to. Once the memory position 94 is set, operation of an AUTO key allows the specimen to be rapidly advanced to the memory position, (if the current position of the specimen is anywhere behind the memory position), or rapidly retracted from the current specimen position (if the current position of the specimen is at or in front of the memory position), to a load/unload position 96. The amount retracted behind the memory position, i.e. the location of the load/unload position 96, may be set by the user. Indicators on the keys advise whether a memory position has been set, and whether the specimen is at or in front of this position or behind the memory position. The control means allows the tube 50, and with it the plate 90 and specimen 92, to be retracted further, when required, to a reset position 98.

The following summary will assist in an appreciation of the preferred embodiment of the invention described above with reference to the drawings. The following are the four features of the preferred embodiment considered the most significant.

Fixed Knife Position—the specimen must always move to the knife and the distance will vary according to the specimen/block size and must accommodate the largest block depth, this is true of other, known, microtomes but the distance to be moved can be varied by moving the knife towards the specimen and re-clamping. The main advantages of fixing the knife position are rigidity when sectioning and ease of cleaning the instrument.

Knife Angle Position Memory—the chosen knife angle for sectioning can be retained when the knife holder is moved or removed and replaced. Different angles are required for the various blades and knives used to compensate for different facet angles, embedding mediums and materials to be sectioned. Routine use requires the setting of only one angle on the knife holder which can be "remembered" when the knife holder is removed for cleaning or replaced with an alternative holder. The fixed knife position feature means that only the knife holder is removed whereas most microtomes have a removable base which means that the base and top are removed together hence retaining the knife angle position.

Auto Load Feature—this feature enables the rapid positioning of the specimen from the loading/unloading position to the trimming/sectioning position. The fixed knife position feature means that the specimen must always move to the knife and the autoload feature speeds up the processing between blocks when the correct memory position is set, and should ensure no clashes between block and knife.

Specimen Tube Mounting Arrangement—this feature enables the stability of the specimen to be maintained for sectioning over the full travel of the specimen tube. The fixed knife position feature requires the specimen to be moved to the knife. To enable a range of block depths to be sectioned enough specimen travel must be allowed between specimen and knife position. This implies that the specimen is being sectioned very often with the specimen tube near full extension, so that it is necessary for stability to be maintained.

The above features are interrelated in that the last three features noted are particularly advantageous in conjunction with the fixed knife position feature, but each such feature can also stand alone.

The fixed knife position feature referred to means that the knife holder base is fixedly attached to the structure of the microtome.

The knife holder base is the platform for mounting a range of knife holders and its stability is critical to the sectioning performance of the microtome. By bolting down this part to the microtome, for example, the knife holder mounted on it is more stable leading to improved sectioning performance.

Other, known, microtomes have a knife holder or knife holder base that can be moved forward and backward relative to the specimen on a track or dovetail to which it is then clamped.

The angular adjustability of the knife holder 12 on knife holder base 11 allows a range of knife holders 12 to be attached to the base and angled to achieve optimum sectioning performance, with the cutting point of the blade at the centre of the radius and hence always at a fixed position on the microtome.

The knife angle position memory feature enables a chosen knife angle to be set on the knife holder such that when it is removed and replaced it can easily be reset to the same angle.

A knife holder, whether it be for disposable blades or solid knives, can be typically set across a wide angle. Those on the preferred embodiment allow 15 degrees of adjustment. This range is available to accommodate different types of blades and knives which can have a range of facet angles for the knife edge. Different facet angles typically require the knife to be set at different angles to the specimen to be sectioned. If the wrong knife angle is set on the knife holder it may have a detrimental effect on the sectioning performance.

A microtome user will typically use one blade/knife type for the majority or work. The user will set the knife angle position memory feature to suit this blade/knife type.

At the end of a sectioning session there will be much debris from the sectioning process around the knife area. It is usual to remove the knife holder to allow better access for cleaning. Another reason for removing the knife holder may be to fit another type. If there were no position memory feature when the knife holder was replaced the angle would have to be reset by remembering what the correct angle setting is or else by carrying out some sectioning and adjusting the angle to suit. The knife angle position memory feature on the other hand enables the correct knife angle to be easily reset.

The preferred embodiment of microtome described with reference to, and shown in, the accompanying drawings, can be used with a range of knife holders which all fit on one common knife holder base on the instrument. The different knife holders hold different types of knives which are used for sectioning different specimen types.

On the majority of known microtomes, as well as angular adjustment of the knife holder being possible, the knife holder base can normally be slid forwards and backwards for additional adjustment. This generally means that the knife holder base can be removed, with the knife holder still attached, by sliding it off the end of its adjustment guides. The knife can therefore be removed and replaced without changing the knife angle. This is not possible with the preferred embodiment of the invention since the knife holder base is permanently fixed to the instrument. The knife holder can therefore only be removed by separating it from the knife holder base which, but for the knife angle position memory feature described, would mean that the knife angle setting would be lost.

In the preferred embodiment, in order to save the knife angle once the knife holder has been set to the required position and locked in position, the screw 43 in the side of the knife holder is released using an Allen key and the screw and with it the block 41 carrying the spring plunger 47, 49, is slid along its slot until the ball spring plunger 49 is felt to engage in the knife holder base slot, after which the screw 43 is re-tightened.

The specimen tube mounting arranged used in the preferred embodiment enables the stability of the specimen to be maintained for sectioning over the full operating travel of the specimen tube. As noted above, in the preferred form of the microtome, the specimen to be sectioned is mounted, by means of a vice and orientation head, on a mounting plate secured to the specimen tube. The movement of the specimen tube backwards and forwards controls the thickness of sections produced by the instrument. The stability of the specimen tube within the instrument is critical to the production of good quality sections. Any large deflections in the specimen tube due to cutting forces can have a detrimental effect on sectioning performance.

The mounting method described with reference to the drawings ensures that the tube 50 is still held rigid when it is fully advanced. This is particularly necessary for the preferred embodiment as the knife position is fixed. The specimen must be advanced to the knife and so there is no way of controlling how far the specimen tube is advanced. Other, known, microtomes typically have a movable knife holder so that the knife can be moved to the specimen and hence sectioning can take place with the tube extended a minimum amount.

What is claimed is:

1. A microtome comprising:
   a knife holder and a knife holder support having cooperating arcuate bearing surfaces permitting angular movement of the knife holder relative to the knife holder support about the axis of curvature of said bearing surfaces with concomitant sliding movement of one of said arcuate surfaces over the other;
   a releaseable securing means operable to pull the knife holder against the knife holder support and thereby to fixedly secure the knife holder on the knife holder support, wherein the releaseable securing means is releaseable to allow angular movement of the knife holder relative to the knife holder support; and
   a locating device adjustably secured to one of the knife holder and knife holder support, and a datum being provided on the other of the knife holder and knife holder support for cooperation with said locating device, such that said locating device engages in said datum to ensure that with said locating device fixed to said one of said knife holder and knife holder support the angular position of the knife holder on the knife holder support at which said locating device cooperates with said datum can readily be established, and said locating device can be fixed in such adjusted position independently of whether or not said releaseable securing means is released or whether or not the knife holder is removed from the knife holder support.

2. A microtome comprising:

a knife holder and a knife holder support having cooperating arcuate bearing surfaces permitting angular movement of the knife holder relative to the knife holder support about the axis of curvature of said bearing surfaces with concomitant sliding movement of one of said arcuate surfaces over the other;

releasable securing means operable to pull the knife holder against the knife holder support and thereby to fixedly secure the knife holder on the knife holder support, said releasable securing means being releasable to allow angular movement of the knife holder relative to the knife holder support; and a locating device carried by the knife holder that can be adjusted in position relative to the knife holder about the axis of curvature of said one of said bearing surfaces, and that can be fixed in such adjusted position relative to the knife holder independently of whether or not said releasable securing means is released or whether or not the knife holder is removed from the knife holder support, said locating device having a projecting element for engagement in a pit or slot provided on the knife holder support to ensure that with said locating device fixed to said knife holder, the angular position of the knife holder on the knife holder support at which said locating device engages in said pit or slot can readily be established, with said releasable securing means released, by rotating the knife holder on the knife holder support until said projecting element engages in said pit or slot, whereafter the releasable securing means can be operated to secure the knife holder in said angular position.

3. A microtome comprising:

a knife holder and a knife holder support having cooperating arcuate bearing surfaces permitting angular movement of the knife holder relative to the knife holder support about the axis of curvature of said bearing surfaces with concomitant sliding movement of one of said arcuate surfaces over the other, wherein a locating device is adjustably secured to the knife holder for cooperation with a datum provided on the knife holder support, to ensure that with said locating device fixed to said knife holder, the angular position of the knife holder on the knife holder support at which said locating device cooperates with said datum can readily be established; and wherein the knife holder has a lateral face perpendicular to the axis of curvature of said bearing surface of the knife holder and a slot is formed in the arcuate bearing surface of the knife holder adjacent said lateral face thereof, the slot having opposing side walls parallel with said lateral face, and a bottom wall which is arcuate with an axis of curvature coincident with the axis of curvature of the bearing surface of the knife holder, the knife holder providing a knife holder wall defined between said lateral face and said slot formed in the arcuate bearing surface and wherein a further slot, which is also arcuate with a centre of curvature on the axis of curvature of said bearing surface, is formed through said knife holder wall and wherein said locating device includes a slider block received in said slot in the bearing surface and having a screw-threaded bore therein, a screw-threaded bolt extending through said arcuate slot in said knife holder wall and in screw-threaded engagement with said screw-threaded bore, the bolt having a head, whereby the slider block can be fixed in position in said slot in the bearing surface by screwing up the bolt until said knife holder wall is clamped between said slider block and the head of said bolt.

4. The microtome according to claim 3, wherein said locating device includes a detent mounted in said slider block and said datum comprises a pit or groove in the arcuate surface of the knife holder support, said pit or groove extending longitudinally parallel with said axis of curvature.

5. The microtome according to claim 4, wherein said slider block does not project from the arcuate surface of the knife holder and said detent is urged away from the axis of curvature of the arcuate surface of the knife holder, towards the knife holder support, by spring means mounted in said slider block, and is displaceable towards the axis of curvature away from the knife holder support against the bias of said spring means.

6. The microtome according to claim 3, wherein said datum comprises a groove in the arcuate surface of the knife holder support, said pit or groove extending longitudinally parallel with said axis of curvature.

7. A microtome comprising:

a knife holder and a knife holder support having cooperating arcuate bearing surfaces permitting angular movement of the knife holder relative to the knife holder support about the axis of curvature of said bearing surfaces with concomitant sliding movement of one of said arcuate surfaces over the other, wherein a locating device is adjustably secured to the knife holder support for cooperation with a datum provided on the knife holder to ensure that with said locating device fixed to said knife holder support, the angular position of the knife holder on the knife holder support at which said locating device cooperates with said datum can readily be established; and wherein the knife holder support has a lateral face perpendicular to the axis of curvature of said bearing surface of the knife holder support and a slot is formed in the arcuate bearing surface of the knife holder support adjacent said lateral face thereof, the slot having opposing side walls parallel with said lateral face, and a bottom wall which is arcuate with an axis of curvature coincident with the axis of curvature of the bearing surface of the knife holder support, the knife holder support providing a knife holder support side wall defined between said lateral face and said slot formed in the arcuate bearing surface and wherein a further slot, which is also arcuate with a centre of curvature on the axis of curvature of said bearing surface, is formed through said knife holder wall and wherein said locating device includes a slider block received in said slot in the bearing surface and having a screw-threaded bore therein, a screw-threaded bolt extending through said arcuate slot in said side wall and in screw-threaded engagement with said screw-threaded bore, the bolt having a head, whereby the slider block can be fixed in position in said slot in the bearing surface by screwing up the bolt until said knife holder support side wall is clamped between said slider block and the head of said bolt.

8. The microtome according to claim 7, wherein said locating device includes a detent mounted in said slider block and said datum comprises a pit or groove in the arcuate surface of the knife holder, said pit or groove extending longitudinally parallel with said axis of curvature.

9. The microtome according to claim 8, wherein said slider block does not project from the arcuate surface of the knife holder support and said detent is urged towards the knife holder by spring means mounted in said slider block and is displaceable away from the knife holder against the bias of said spring means.

10. The microtome according to claim 7, wherein said datum comprises a groove in the arcuate surface of the knife holder, said pit or groove extending longitudinally parallel with said axis of curvature.

* * * * *